(12) United States Patent
Penders et al.

(10) Patent No.: US 10,595,786 B2
(45) Date of Patent: *Mar. 24, 2020

(54) CONFIDENCE INDICATOR FOR PHYSIOLOGICAL MEASUREMENTS USING A WEARABLE SENSOR PLATFORM

(71) Applicant: Samsung Electronics Co., Ltd., Gyeonggi-do (KR)

(72) Inventors: Julien Penders, Liege (BE); Alexander Young, Eindhoven (NL); Noam Rosenthal, Amsterdam (NL); Ram Fish, San Jose, CA (US); Eva C. Wentink, Eindhoven (NL)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/290,802

(22) Filed: Mar. 1, 2019

(65) Prior Publication Data

US 2019/0192080 A1 Jun. 27, 2019

Related U.S. Application Data

(63) Continuation of application No. 14/286,846, filed on May 23, 2014, now Pat. No. 10,258,288.
(Continued)

(51) Int. Cl.
*A61B 5/00* (2006.01)
*A61B 5/0205* (2006.01)
(Continued)

(52) U.S. Cl.
CPC ............. *A61B 5/721* (2013.01); *A61B 5/681* (2013.01); *A61B 5/7221* (2013.01);
(Continued)

(58) Field of Classification Search
CPC ....... A61B 5/721; A61B 5/681; A61B 5/7221; A61B 5/7246; A61B 5/743; A61B 5/7455;
(Continued)

(56) References Cited

U.S. PATENT DOCUMENTS

| 8,290,559 B2 | 10/2012 | Shariati |
| 2002/0035315 A1 | 3/2002 | Ali |

(Continued)

FOREIGN PATENT DOCUMENTS

| CN | 101340846 A | 1/2009 |
| TW | 447215 U | 2/2013 |
| WO | 2013030744 A1 | 3/2013 |

OTHER PUBLICATIONS

Lachambre et al., "Distinguishing monophonies from polyphonies using Weibull bivariate distributions," IRIT University of Toulouse, France.

*Primary Examiner* — John E Breene
*Assistant Examiner* — L. Anderson
(74) *Attorney, Agent, or Firm* — Van Pelt, Yi & James LLP

(57) ABSTRACT

Embodiments include a method and system for providing data to a user of a wearable sensor platform. The method may be performed by a least one software component executing on at least one processor. The method includes capturing data for the user using at least one sensor in the wearable sensor platform. The data includes physiological data and artifact data. The physiological data includes noise data therein. A confidence indicator for the data is determined based on at least one of the physiological data and the artifact data. A physiological data signal corresponding to the physiological data and the confidence indicator is provided to the user on the wearable device platform.

15 Claims, 10 Drawing Sheets

Related U.S. Application Data

(60) Provisional application No. 61/969,769, filed on Mar. 24, 2014.

(51) Int. Cl.
*A61B 5/0402* (2006.01)
*A61B 5/11* (2006.01)
*A61B 5/053* (2006.01)

(52) U.S. Cl.
CPC ......... *A61B 5/0059* (2013.01); *A61B 5/02055* (2013.01); *A61B 5/0402* (2013.01); *A61B 5/0533* (2013.01); *A61B 5/11* (2013.01); *A61B 5/7246* (2013.01); *A61B 5/743* (2013.01); *A61B 5/7405* (2013.01); *A61B 5/746* (2013.01); *A61B 5/7455* (2013.01); *A61B 5/7475* (2013.01)

(58) Field of Classification Search
CPC ... A61B 5/746; A61B 5/02055; A61B 5/0402; A61B 5/11
See application file for complete search history.

(56) References Cited

U.S. PATENT DOCUMENTS

| | | |
|---|---|---|
| 2003/0101027 A1 | 5/2003 | Weber |
| 2008/0081973 A1 | 4/2008 | Hoarau |
| 2011/0213271 A1 | 9/2011 | Telfort |
| 2012/0041316 A1 | 2/2012 | Ali |
| 2012/0165631 A1 | 6/2012 | Diab |
| 2012/0203087 A1 | 8/2012 | McKenna |
| 2013/0131475 A1 | 5/2013 | Eisen |
| 2014/0200423 A1 | 7/2014 | Eisen |
| 2015/0230756 A1* | 8/2015 | Luna .................. A61B 5/02438 600/484 |

* cited by examiner

CONFIDENCE INDICATOR FOR PHYSIOLOGICAL MEASUREMENTS USING A WEARABLE SENSOR PLATFORM

CROSS-REFERENCE TO RELATED APPLICATIONS

This application is a continuation of co-pending U.S. patent application Ser. No. 14/286,846, entitled CONFIDENCE INDICATOR FOR PHYSIOLOGICAL MEASUREMENTS USING A WEARABLE SENSOR PLATFORM, filed May 23, 2014, which claims priority to U.S. Provisional Patent Application No. 61/969,769, entitled ADAPTIVE SYSTEM BASED ON CONFIDENCE INDICATOR, filed Mar. 24, 2014, both of which are incorporated herein by reference for all purposes.

BACKGROUND

Physiological measurements collect data for various processes occurring in a living body. For example, an electrocardiogram (ECG) measures electrical potentials produced through cardiac activity at the body surface and may be used to interpret various aspects related to cardiac activity. Bioimpedance is a measure of the resistance of living tissue to a current driven through the tissue and may be used to determine blood volume pulsed through an artery. Temperature may also be measured at the body surface and may be indicative of general health.

One challenge faced when making physiological measurements is noise introduced by non-physiological influences. Motion of the human body is one source of such noise. For example, an ECG reading is typically acquired using electrodes placed on a user's skin. A motion artifact is noise that results from motion of the electrode in relation to the user's skin. In some cases, movement of the electrode deforms the skin around the electrode site. This deformation causes a change in the electrical characteristics of the skin around the electrode and may contribute to the ECG reading. This contribution is not related to cardiac activity and thus is a source of noise. Motion artifacts are particularly relevant for physiological measurements in a mobile or portable application. For such applications, a high level of noise may be introduced by motion artifacts.

Accordingly, what is desired is a system and method to aid in accounting for noise such as motion artifacts in physiological measurements, particularly in portable applications.

BRIEF SUMMARY

Embodiments include a method and system for providing data to a user of a wearable sensor platform. The method may be performed by a least one software component executing on at least one processor. The method includes capturing data for the user using at least one sensor in the wearable sensor platform. The data includes physiological data and artifact data. The physiological data has noise data therein. A confidence indicator for the data is determined based on at least one of the physiological data and the artifact data. A physiological data signal corresponding to the physiological data and the confidence indicator is provided to the user on the wearable device platform.

Figure 1:
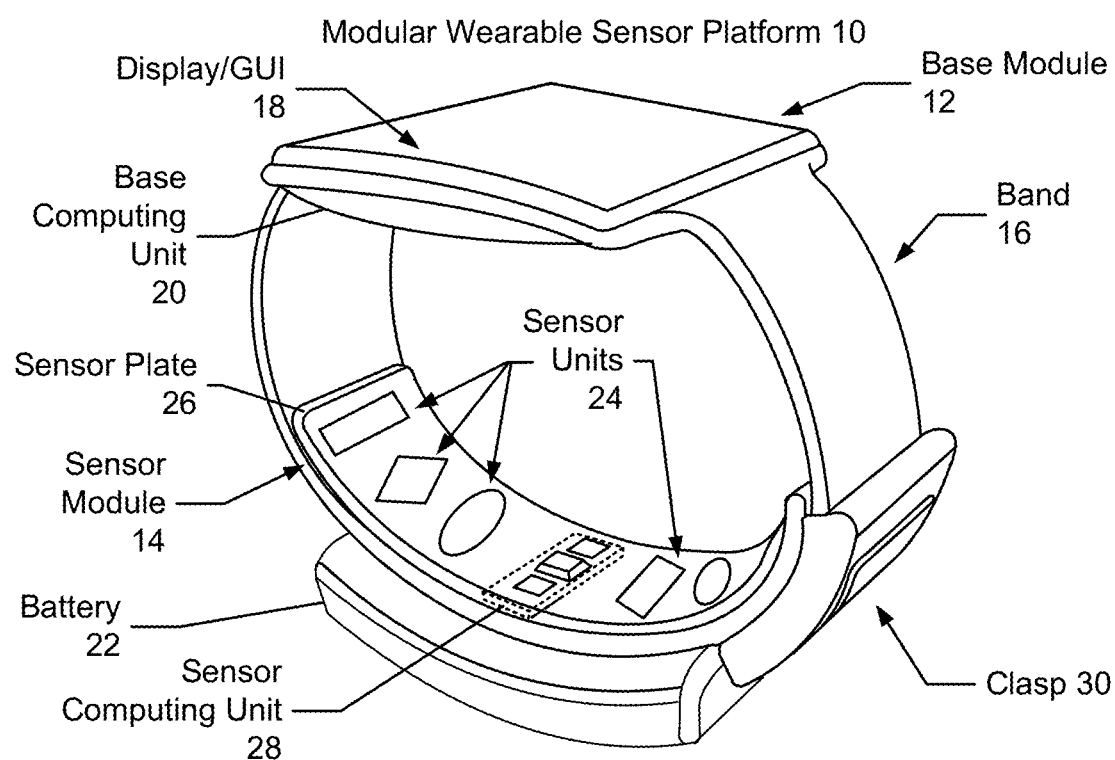
FIG. 1 is a diagram illustrating an exemplary embodiment of a modular sensor platform.

For the purpose of illustrating the general inventive concept of the invention, certain embodiments are shown in the drawings. It should be understood, however, that the present invention is not limited to the arrangements and instrumentality shown in the attached drawings.

DETAILED DESCRIPTION

The embodiments described herein relate to measuring and providing physiological data to a user of a wearable sensor platform. The following description is presented to enable one of ordinary skill in the art to make and use the invention and is provided in the context of a patent application and its requirements. Various modifications to the exemplary embodiments and the generic principles and features described herein will be readily apparent. Reference is made in detail to the embodiments of the present general inventive concept, examples of which are illustrated in the accompanying drawings, wherein like reference numerals refer to the like elements throughout. The embodiments are described below in order to explain the present general inventive concept while referring to the figures.

Reference will now be made in detail to the embodiments of the present general inventive concept, examples of which are illustrated in the accompanying drawings, wherein like reference numerals refer to the like elements throughout. The embodiments are described below in order to explain the present general inventive concept while referring to the figures.

Before any embodiments of the invention are explained in detail, it is to be understood that the invention is not limited in its application to the details of construction and the arrangement of components set forth in the following description or illustrated in the drawings.

Advantages and features of the present invention and methods of accomplishing the same may be understood more readily by reference to the following detailed description and the drawings. The present general inventive concept may, however, be embodied in many different forms of being practiced or of being carried out in various ways and should not be construed as being limited to the embodiments set forth herein. Rather, these embodiments are provided so that this disclosure will be thorough and complete and will fully convey the general inventive concept to those skilled in the art, and the present general inventive concept is defined by the appended claims. In the drawings, the thickness of layers and regions are exaggerated for visual clarity.

Also, the phraseology and terminology used in this document are for the purpose of description and should not be regarded as limiting. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

As should also be apparent to one of ordinary skill in the art, the systems shown in the figures are models of what actual systems might be like. Some of the modules and logical structures described are capable of being implemented in software executed by a microprocessor or a similar device, or of being implemented in hardware using a variety of components including, for example, application specific integrated circuits ("ASICs"). A term like "processor" may include or refer to both hardware and/or software. No specific meaning is implied or should be inferred simply due to the use of capitalization.

Likewise, the term "component" or "module", as used herein, means, but is not limited to, a software or hardware component, such as a field programmable gate array (FPGA) or ASIC, which performs certain tasks. A component or module may advantageously be configured to reside in the addressable storage medium and configured to execute on one or more processors. Thus, a component or module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for the components and components or modules may be combined into fewer components and components or modules or further separated into additional components and components or modules.

Unless defined otherwise, all technical and scientific terms used herein have the same meaning as commonly understood by one of ordinary skill in the art to which this invention belongs. Further, unless defined otherwise, all terms defined in generally used dictionaries should have their ordinary meaning. It is noted that the use of any and all examples, or exemplary terms provided herein is intended merely to better illuminate the general inventive concept and is not a limitation on the scope of the invention unless otherwise specified.

Figure 2:
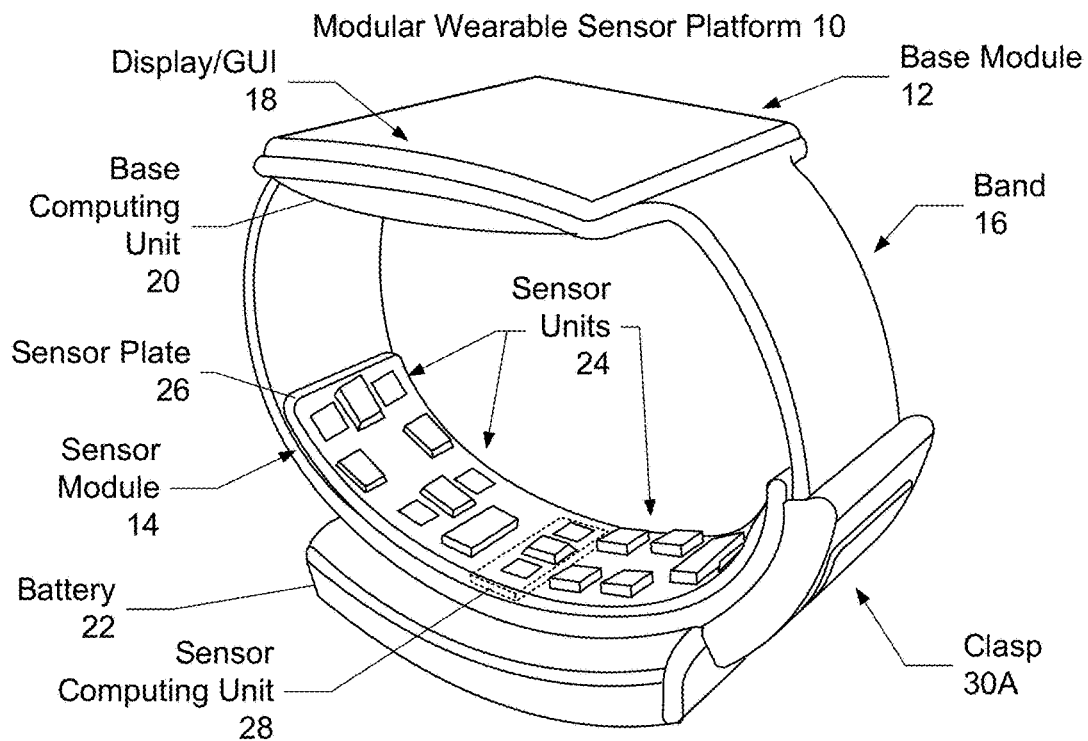
FIG. 2 is an exemplary embodiment of the modular sensor platform of FIG. 1.
Figure 3:
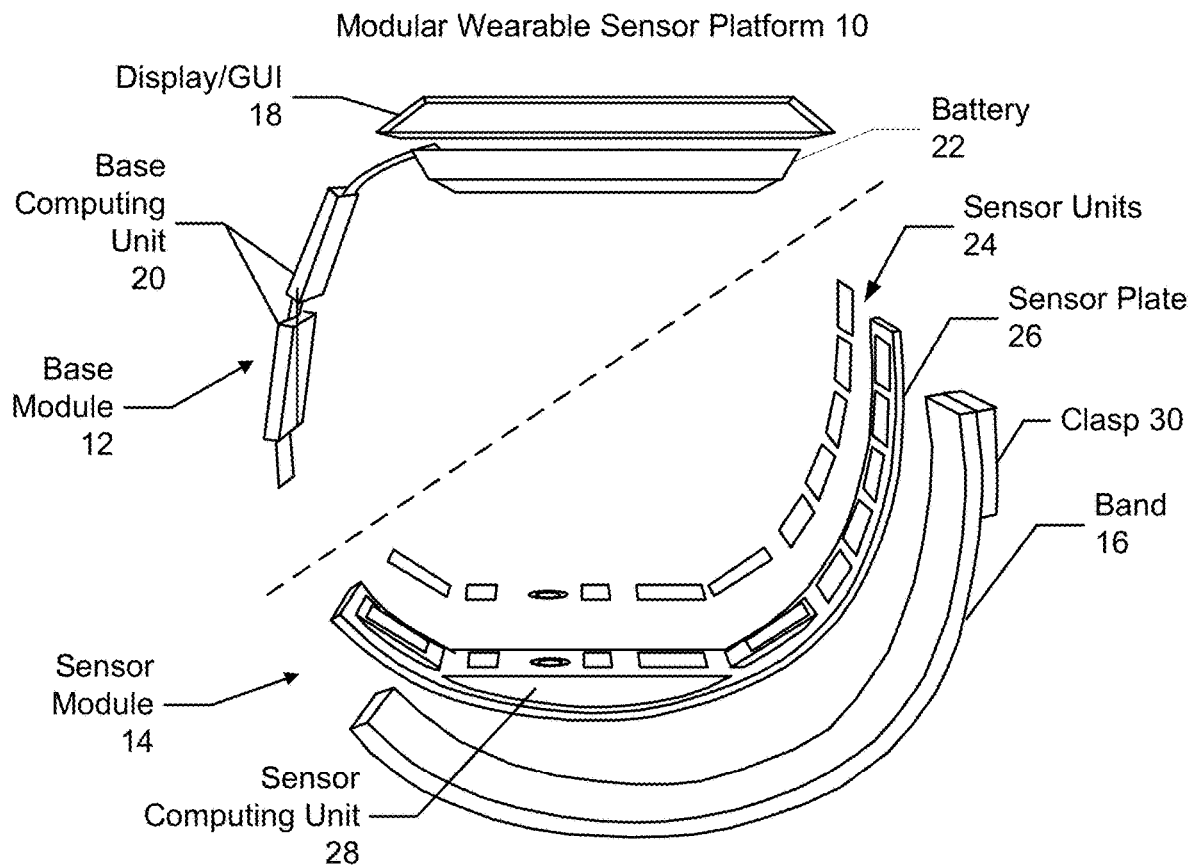
FIG. 3 is a diagram illustrating another exemplary embodiment of a modular sensor platform.

FIGS. 1 and 2 are diagrams illustrating embodiments of a modular wearable sensor platform. FIGS. 1 and 2 depict a perspective view of embodiments of the wearable sensor platform 10, while FIG. 3 depicts an exploded side view of another embodiment of the wearable sensor platform 10. Although the components of the wearable sensor platform in FIGS. 1 and 2 may be substantially the same, the locations of modules and/or components may differ.

In the embodiment shown in FIGS. 1 and 2, the wearable sensor platform 10 may be implemented as a smart watch or other wearable device that fits on part of a body, here a user's wrist 11.

The wearable sensor platform 10 may include a base module 12, a band 16, a clasp 30/30A, a battery 22 and a sensor module 14 coupled to the band 16. In some embodiments, the modules and/or components of the wearable sensor platform 10 may be removable by an end user (e.g., a consumer, a patient, a doctor, etc.). However, in other embodiments, the modules and/or components of the wearable sensor platform 10 are integrated into the wearable sensor platform 10 by the manufacturer and may not be intended to be removed by the end user. The wearable sensor platform 10 may be waterproof or water sealed.

The band or strap 16 may be one piece or modular. The band 16 may be made of a fabric. For example, a wide range of twistable and expandable elastic mesh/textiles are contemplated. The band 16 may also be configured as a multi-band or in modular links. The band 16 may include a latch or a clasp mechanism to retain the watch in place in certain implementations. In certain embodiments, the band 16 will contain wiring (not shown) connecting, among other things, the base module 12 and sensor module 14. Wireless communication, alone or in combination with wiring, between base module 12 and sensor module 14 is also contemplated.

The sensor module 14 may be removably attached on the band 16, such that the sensor module 14 is located at the bottom of the wearable sensor platform 10 or, said another way, on the opposite end of the base module 12. Positioning the sensor module 14 in such a way to place it in at least partial contact with the skin on the underside of the user's wrist 11 to allow the sensor units 24 to sense physiological data from the user. The contacting surface(s) of the sensor units 24 may be positioned above, at or below, or some combination such positioning, the surface of the sensor module 14.

The base module 12 attaches to the band 16 such that the base module 12 is positioned at top of the wearable sensor platform 10. Positioning the base module 12 in such a way to place it in at least partial contact with the top side of the wrist.

The base module 12 may include a base computing unit 20 and a display 18 on which a graphical user interface (GUI) may be provided. The base module 12 performs functions including, for example, displaying time, performing calculations and/or displaying data, including sensor data collected from the sensor module 14. In addition to communication with the sensor module 14, the base module 12 may wirelessly communicate with other sensor module(s) (not shown) worn on different body parts of the user to form a body area network, or with other wirelessly accessible devices (not shown), like a smartphone, tablet, display or other computing device. As will be discussed more fully with respect to FIG. 4, the base computing unit 20 may include a processor 202, memory 206, input/output 208, a communication interface 210, a battery 22 and a set of sensors 214, such as an accelerometer/gyroscope 214A and thermometer 214B.

The sensor module 14 collects data (e.g., physiological, activity data, sleep statistics and/or other data), from a user and is in communication with the base module 12. The sensor module 14 includes sensor units 24 housed in a sensor plate 26. For certain implementations, because a portable device, such as a wristwatch, has a very small volume and limited battery power, sensor units 24 of the type disclosed may be particularly suited for implementation of a sensor measurement in a wristwatch. In some embodiments, the sensor module 14 is adjustably attached to the band 16 such that the base module 12 is not fixedly position, but can be configured differently depending on the physiological make-up of the wrist.

The sensor units 24 may include an optical sensor array, a thermometer, a galvanic skin response (GSR) sensor array, a bioimpedance (BioZ) sensor array, an electrocardiogram (ECG) sensor, or any combination thereof. The sensors units 24 may take information about the outside world and supply it to the wearable modular sensor platform 10. The sensors 24 can also function with other components to provide user or environmental input and feedback to a user. For example, an MEMS accelerometer may be used to measures information such as position, motion, tilt, shock, and vibration for use by processor 202. Other sensor(s) may also be employed. The sensor module 14 may also include a sensor computing unit 28. The sensor units 24 may also include biological sensors (e.g., pulse, pulse oximetry, body temperature, blood pressure, body fat, etc.), proximity detector for detecting the proximity of objects, and environmental sensors (e.g., temperature, humidity, ambient light, pressure, altitude, compass, etc.).

In other embodiments, the clasp 30 also provides an ECG electrode. One or more sensor units 24 and the ECG electrode on the clasp 30 can form a complete ECG signal circuit when the clasp 30 is touched. The sensor computing unit 28 may analyze data, perform operations (e.g., calculations) on the data, communicate data and, in some embodiments, may store the data collected by the sensor units 24. In some embodiments, the sensor computing unit 28 receives (for example, data indicative of an ECG signal) from one or more of the sensors of the sensor units 24, and processes the received data to form a predefined representation of a signal (for example, an ECG signal).

The sensor computing unit 28 can also be configured to communicate the data and/or a processed form of the received data to one or more predefined recipients, for example, the base computing unit 20, for further processing, display, communication, and the like. For example, in certain implementations the base computing unit 20 and our sensor computing unit determine whether data is reliable and determine an indication of confidence in the data to the user.

Because the sensor computing unit 28 may be integrated into the sensor plate 26, it is shown by dashed lines in FIGS. 1-2. In other embodiments, the sensor computing unit 28 may be omitted or located elsewhere on the wearable sensor platform 10 or remotely from the wearable sensor platform 10. In an embodiment where the sensor computing unit 28 may be omitted, the base computing unit 20 may perform functions that would otherwise be performed by the sensor computing unit 28. Through the combination of the sensor module 14 and base module 12, data may be collected, transmitted, stored, analyzed, transmitted and presented to a user.

The wearable sensor platform 10 depicted in FIG. 3 is analogous to the wearable sensor platform 10 depicted in FIGS. 1 and 2. Thus, the wearable sensor platform 10 includes a band 12, a battery 22, a clasp 30, a base module 12 including a display/GUI 18, a base computing unit 20, and a sensor module 14 including sensor units 24, a sensor plate 26, and an optional sensor computing unit 28. However, as can be seen in FIG. 3, the locations of certain modules have been altered. For example, the clasp 30 is closer in FIG. 3 to the display/GUI 18 than clasp 34 is in FIG. 1. Similarly, in FIG. 3, the battery 22 is housed with the base module 12. In the embodiment shown in FIG. 1, the battery 22 is housed on the band 16, opposite to the display 18. However, it should be understood that, in some embodiments, the battery 22 charges the base module 12 and optionally an internal battery (not shown) of the base module 12. In this way, the wearable sensor platform 10 may be worn continuously. Thus, in various embodiments, the locations and/or functions of the modules and other components may be changed.

Figure 4:
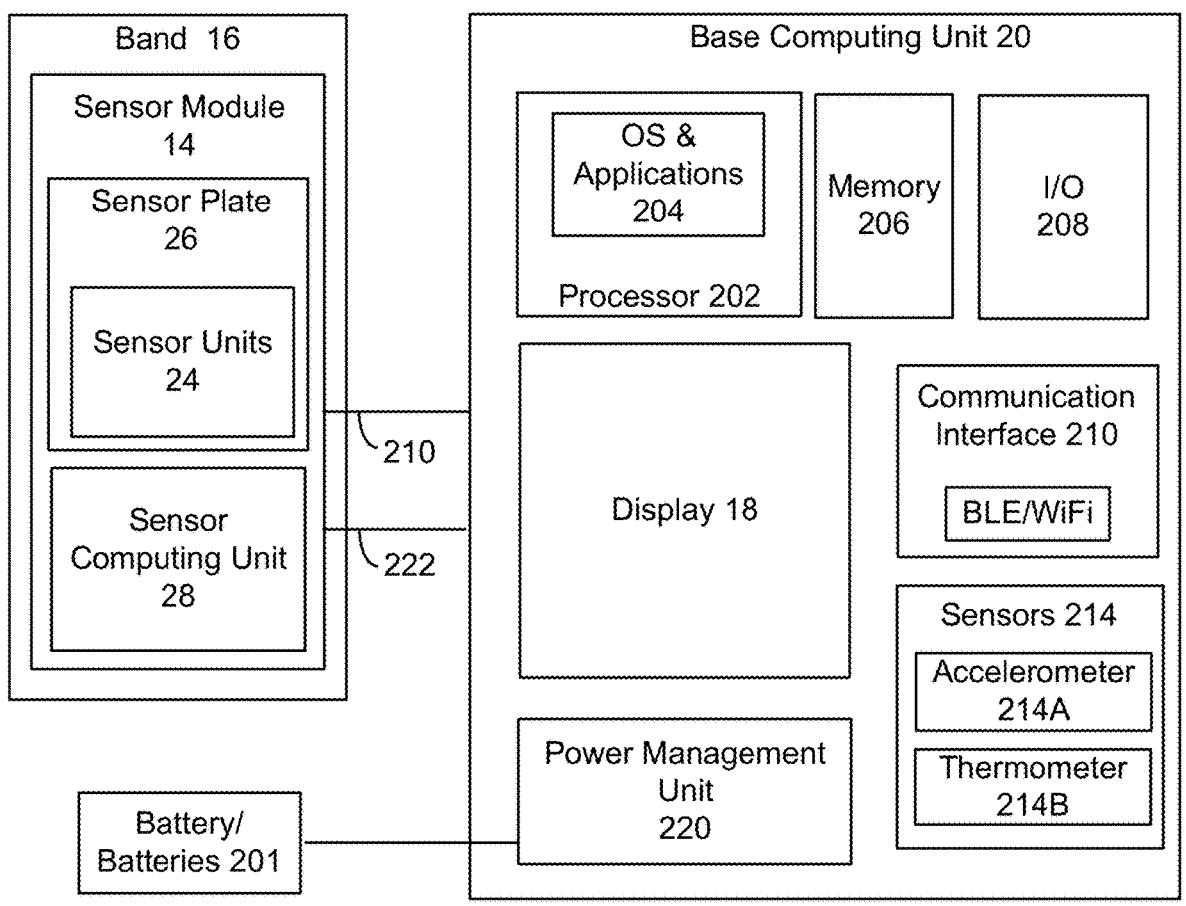
FIG. 4 is a block diagram illustrating an exemplary embodiment of the modular sensor platform, including a bandwidth sensor module in connection with components comprising the base computing unit and battery.

FIG. 4 is a diagram illustrating one embodiment of a modular wearable sensor platform 10 and components comprising the base module 12. The wearable sensor platform 10 is analogous to the wearable sensor platform 10 in FIGS. 1-3 and thus includes analogous components having similar reference labels. In this embodiment, the wearable sensor platform 10 may include a band 16, and a sensor module 14 attached to band 16. The removable sensor module 14 may further include a sensor plate 26 attached to the band 16, and sensor units 24 attached to the sensor plate 26. The sensor module 14 may also include a sensor computing unit 32.

The wearable sensor platform 10 includes a base computing unit 20 in FIG. 4 analogous to the base computing unit 20 and one or more batteries 22 in FIGS. 1-3. For example, permanent and/or removable batteries 22 that are analogous to the battery 22 in FIGS. 1-3 may be provided. In one embodiment, the base computing unit 20 may communicate with or control the sensor computing unit 32 through a communication interface 210. In one embodiment, the communication interface 210 may comprise a serial interface. The base computing unit 20 may include a processor 202, a memory 206, input/output (I/O) 208, a display 18, a communication interface 210, sensors 214, and a power management unit 220.

The processor 202, the memory 206, the I/O 208, the communication interface 210 and the sensors 214 may be coupled together via a system bus (not shown). The processor 202 may include a single processor having one or more cores, or multiple processors having one or more cores. The processor 202 may be configured with the I/O 208 to accept, receive, transduce and process verbal audio frequency command, given by the user. For example, audio codec may be used. The processor 202 may execute instructions of an operating system (OS) and various applications 204. The processor 202 may control on command interactions among device components and communications over an I/O interface. Examples of the OS 204 may include, but not limited to, Linux Android™, and Android Wear.

The memory 206 may comprise one or more memories comprising different memory types, including RAM (e.g., DRAM and SRAM) ROM, cache, virtual memory microdrive, hard disks, microSD cards, and flash memory, for example. The I/O 208 may comprise a collection of components that input information and output information. Example components comprising the I/O 208 having the ability to accept inputted, outputted or other processed data include a microphone, messaging, camera and speaker. I/O 208 may also include an audio chip (not shown), a display controller (not shown), and a touchscreen controller (not shown).

The communication interface 210 may include components for supporting one-way or two-way wireless communications and may include a wireless network interface controller (or similar component) for wireless communication over a network in some implementations, a wired interface in other implementations, or multiple interfaces. In one embodiment, the communication interface 210 is for primarily receiving data remotely, including streaming data, which is displayed and updated on the display 18. However, in an alternative embodiment, besides transmitting data, the communication interface 210 could also support voice transmission. In an exemplary embodiment, the communication interface 210 supports low and intermediate power radio frequency (RF) communications. In certain implementations, example types of wireless communication may include Bluetooth Low Energy (BLE), WLAN (wireless local area network), WiMAX, passive radio-frequency identification (RFID), network adapters and modems. However, in another embodiment, example types of wireless communication may include a WAN (Wide Area Network) interface, Wi-Fi, WPAN, multi-hop networks, or a cellular network such as 3G, 4G, 5G or LTE (Long Term Evolution). Others wireless options may include ultra-wide band (UWB) and infrared, for example. The communication interface 210 may also include other types of communications devices (not shown) besides wireless, such as serial communications via contacts and/or USB communications. For example, a micro USB-type USB, flash drive, or other wired connection may be used with the communication interface 210.

In one embodiment, the display 18 may be integrated with the base computing unit 20; while in another embodiment, the display 18 may be external from the base computing unit 20. Display 18 may be flat or curved, e.g., curved to the approximate curvature of the body part on which the wearable sensor module platform 10 is located (e.g., a wrist, an ankle, a head, etc.).

Display 18 may be a touch screen or gesture controlled. The display 18 may be an OLED (Organic Light Emitting Diode) display, TFT LCD (Thin-Film-Transistor Liquid Crystal Display), or other appropriate display technology. The display 18 may be active-matrix. An example display 18 may be an AMOLED display or SLCD. The display may be 3D or flexible. The sensors 214 may include any type of microelectromechanical systems (MEMs) sensor. Such sensors may include an accelerometer/gyroscope 214A and a thermometer 214B, for instance.

The power management unit 220 may be coupled to the power source 22 and may comprise a microcontroller that communicates and/or controls power functions of at least the base computing unit 20. Power management unit 220 communicates with the processor 202 and coordinates power management. In some embodiments, the power management unit 220 determines if a power level falls below a certain threshold level. In other embodiments, the power management unit 220 determines if an amount of time has elapsed for secondary charging.

The power source 22 may be permanent or removable battery, fuel cell or photo voltage cell, etc. The battery 22 may be disposable. In one embodiment, the power source 22 may comprise a rechargeable, lithium ion battery or the like may be used, for example. The power management unit 220 may include a voltage controller and a charging controller for recharging the battery 22. In some implementations, one or more solar cells may be used as a power source 22. The power source 22 may also be powered or charged by AC/DC power supply. The power source 22 may charge by non-contact or contact charging. In one embodiment, the power management unit 220 may also communicate and/or control the supply of battery power to the removable sensor module 14 via power interface 222. In some embodiments, the battery 22 is embedded in the base computing unit 20. In other embodiments, the battery 22 is external to the base computing unit 20.

Other wearable device configurations may also be used. For example, the wearable sensor module platform can be implemented as an leg or arm band, a chest band, a wristwatch, an article of clothing worn by the user such as a snug fitting shirt, or any other physical device or collection of devices worn by the user that is sufficient to ensure that the sensor units 24 are in contact with approximate positions on the user's skin to obtain accurate and reliable data.

Figure 5:
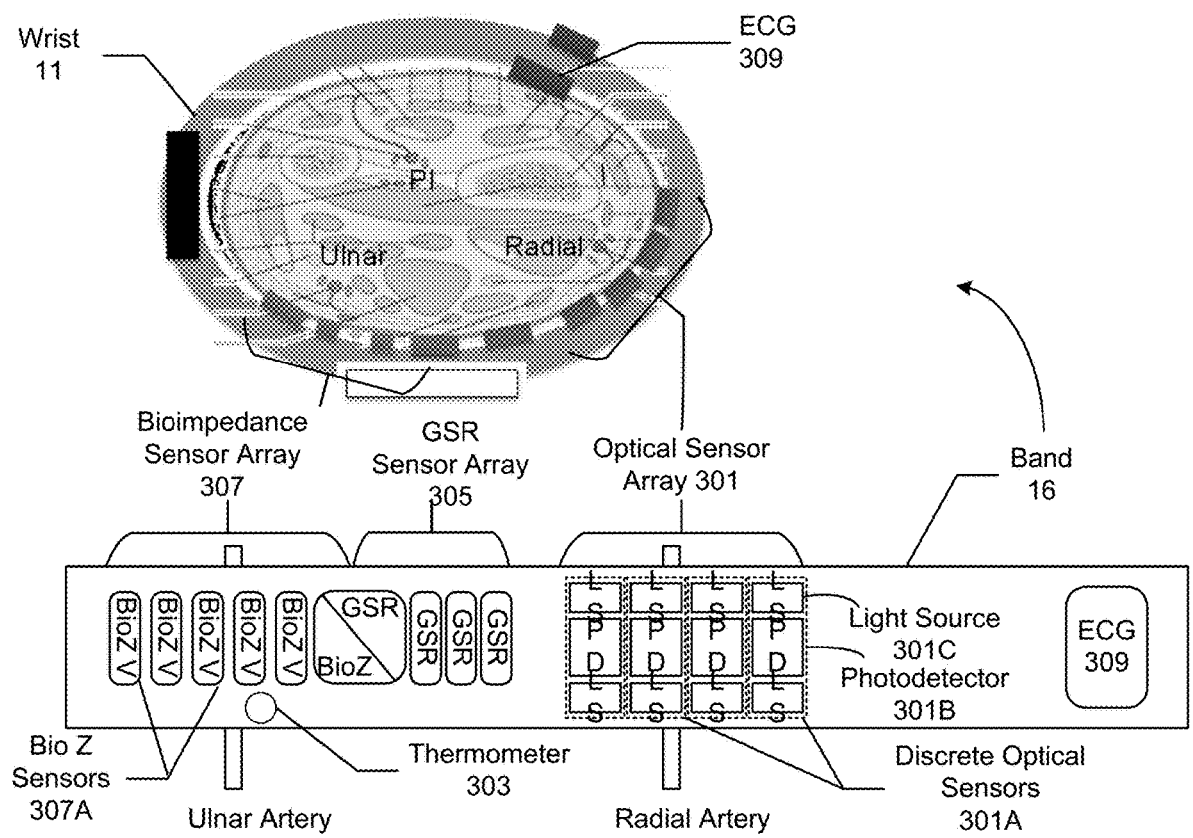
FIG. 5 is a diagram illustrating an exemplary embodiment of a modular sensor platform with a self-aligning sensor array system in relation to use about the wrist.

FIG. 5 is a diagram illustrating an implementation of a wearable sensor module 10. The top portion of FIG. 5 illustrates the wearable sensor module 10 wrapped around a cross-section of a user's wrist 11, while the bottom portion of FIG. 5 shows the band 16 in an flattened position.

According to this embodiment, the wearable sensor module 10 includes at least an optical sensor array 301, and may also include optional sensors, such as a thermometer 303, a galvanic skin response (GSR) sensor array 305, a BioZ sensor array 307, and an electrocardiogram (ECG) sensor 309, other sensor(s) 311 or any combination of which may comprise a sensor array.

According to another embodiment, the sensor units 24 configured as a sensor array(s) comprising an array of discrete sensors that are arranged or laid out on the band 16, such that when the band 16 is worn on a body part, each sensor array may straddle or otherwise addresses a particular blood vessel (i.e., a vein, artery, or capillary), or an area with higher electrical response irrespective of the blood vessel.

More particularly, as can be seen in FIG. 5, the sensor array may be laid out substantially perpendicular to a longitudinal axis of the blood vessel and overlaps a width of the blood vessel to obtain an optimum signal. In one embodiment, the band 16 may be worn so that the sensor units 24 comprising the sensor array(s) contact the user's skin, but not so tightly that the band 16 is prevented from any movement over the body part, such as the user's wrist 11, or creates discomfort for the user at sensor contact points.

In another embodiment, the sensor units 24 may comprise an optical sensor array 301 may comprise a photoplethysmograph (PPG) sensor array that may measures relative blood flow, pulse and/or blood oxygen level. In this embodiment, the optical sensor array 301 may be arranged on sensor module 14 so that the optical sensor array 301 is positioned in sufficient proximity to an artery, such as the radial or ulnar artery, to take adequate measurements with sufficient accuracy and reliability.

Further details of the optical sensor array 301 will now be discussed. In general, configuration and layout of each of the discrete optical sensors 301A may vary greatly depending on use cases. In one embodiment, the optical sensor array 301 may include an array of discrete optical sensors 301A, where each discrete optical sensor 301A is a combination of at least one photodetector 301B and at least two matching light sources located adjacent to the photodetector 301B. In one embodiment, each of the discrete optical sensors 301A may be separated from its neighbor on the band 16 by a predetermined distance of approximately 0.5 to 2 mm.

In one embodiment, the light sources 301C may each comprise light emitting diode (LED), where LEDs in each of the discrete optical sensors emit a light of a different wavelength. Example light colors emitted by the LEDs may include green, red, near infrared, and infrared wavelengths. Each of the photodetectors 301B convert received light energy into an electrical signal. In one embodiment, the signals may comprise reflective photoplethysmograph signals. In another embodiment, the signals may comprise transmittance photoplethysmograph signals. In one embodiment, the photodetectors 301B may comprise phototransistors. In alternative embodiment, the photodetectors 301B may comprise charge-coupled devices (CCD).

According to an exemplary embodiment of an adjustable sensor support structure, a series of sensors supported by flexible bridge structures may be serially connected edge-to-edge along a band. Such a band with bridge supported sensors may be worn, for example, about the wrist. When worn about a measurement site such as the wrist, the varying topology of the wrist may cause force(s) to simultaneously be exerted upon the bridges due to compliance of the band to the varying topology of the wrist.

Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other. Various cloud-based platforms and/or other database platforms may be employed in certain implementations of the modular sensor platform 10 to, for example, receive and send data to the modular sensor platform 10.

Figure 6:
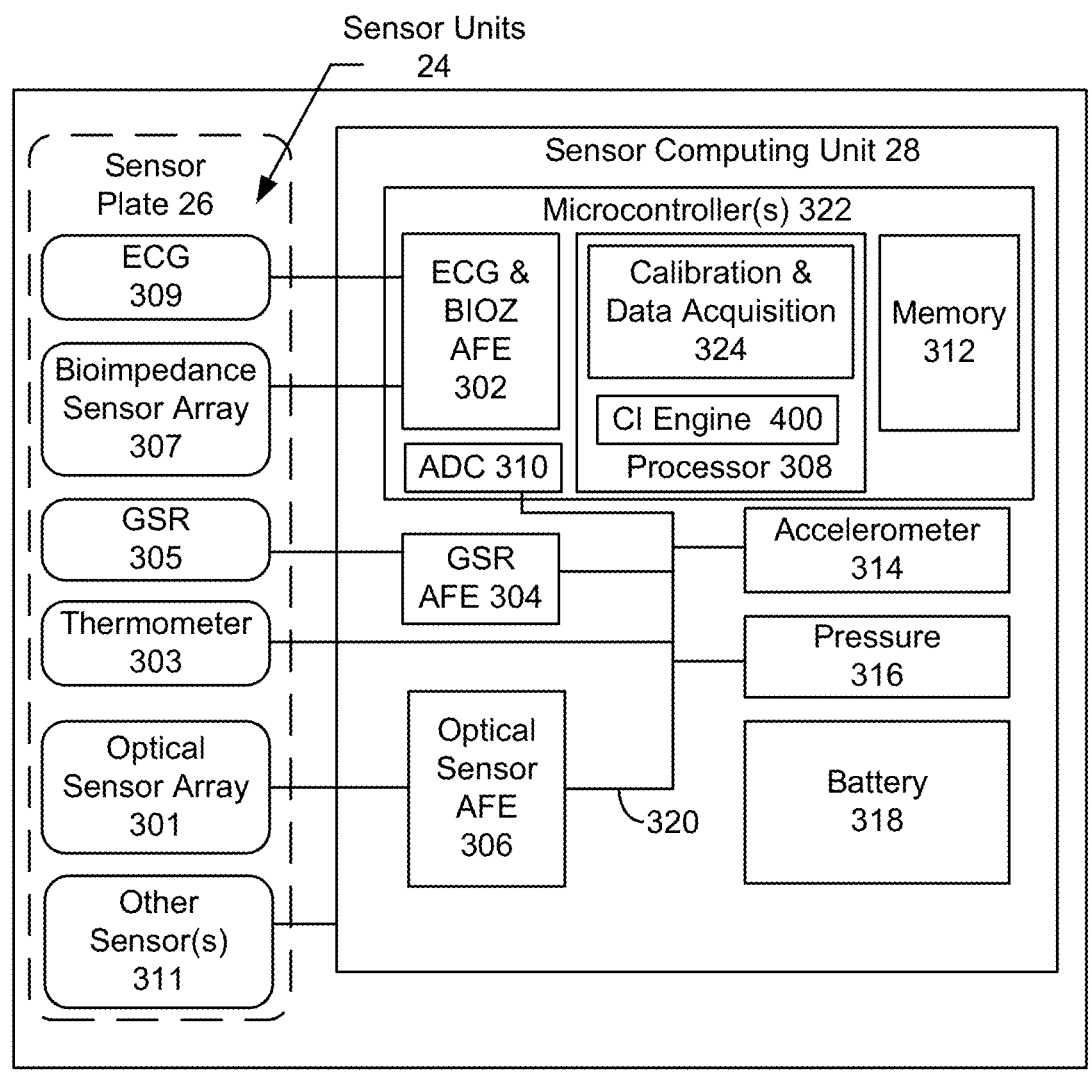
FIG. 6 is a block diagram of an exemplary embodiment of a sensor module.

FIG. 6 is a block diagram illustrating components of an embodiment of a sensor module 14. The sensor module 14 is analogous to the sensor modules 14 and thus includes analogous components having similar labels. As described above, the sensor module 14 may include sensor units 24 affixed to a sensor plate 26, and a sensor computing unit 28. In the embodiment shown, the sensor units 24 may include an optical sensor array 301, a thermometer 303, a GSR sensor array 305, a BioZ sensor array 307, and an ECG sensor 309, other sensor(s) 311 and/or any combination thereof. Although a particular number sensors and sensor arrays are shown, another number of sensors/sensor arrays and/or different sensors/sensor arrays may be included. The sensors and/or arrays may be affixed to the sensor plate 26 or the band 16.

In one embodiment, the optical sensor array 301 may comprise a photoplethysmograph (PPG) sensor array that may measure relative blood flow, pulse and/or blood oxygen level. In one embodiment, the optical sensor array 12 may include an array of discrete optical sensors, where each discrete optical sensor is a combination of at least one photodetector and at least two matching light sources (e.g., LEDs) located adjacent to the photodetector. In this embodiment, the optical sensor array 301 may be arranged on the band so that the optical sensor array 301 straddles a blood vessel, such as the radial artery or the ulnar artery.

The thermometer 303 may measure temperature or a temperature gradient. The galvanic skin response (GSR) sensor array 305 may comprise four or more GSR sensors that may measure electrical conductance of the skin that varies with moisture level. The bioimpedance (BioZ) sensor array 307 may comprise four or more bioimpedance sensors that measure bioelectrical impedance or opposition to a flow of electric current through the tissue. In other embodiments, the arrays 305 and/or 307 may have another number of sensors. In the embodiment shown, the bioimpedance sensor array 16 may be arranged or positioned on the band to straddle a blood vessel, such as the Radial or Ulnar artery. In one embodiment, one or more electrodes comprising the bioimpedance sensors may be multiplexed with one or more of the GSR sensors 305. The electrocardiography sensors (ECG) sensor 309 may measure electrical activity of the user's heart over a period of time.

In one embodiment, the ECG 309, the bioimpedance sensor array 307, the GSR 305, the thermometer 303, the optical sensor array 301 and other sensor(s) 311 may be coupled to the sensor computing unit 28 that controls and receives data from the sensor units 24. In one embodiment, the sensor computing unit 28 may be part of the band 16 (not shown). In another embodiment, the sensor computing unit 28 may be part of the sensor plate 26. In other embodiments, the sensor computing unit 28 may be omitted in favor of the base computing unit 20. In such embodiments, the functions described herein as being carried out by the sensor computing unit 28 may be performed by the base computing unit 20.

The sensor computing unit 28 may include an ECG and bioimpedance (BIOZ) analog front end (AFE) 302, a GSR AFE 304, an optical sensor AFE 306, a processor 308, and analog-to-digital converter (ADC) 310, a memory 312, a three-axis accelerometer 314, a pressure sensor 316 and a battery 318. In some embodiments, the battery 318 may be replaced by the battery 22. In addition, the accelerometer 314 may be within the sensor computing unit 28, part of the base computing 20 or in another location on the wearable sensor platform 10.

As used herein, an AFE may include an analog signal conditioning circuitry interface between corresponding sensors and the ADC 310 or the processor 308. The ECG and BIOZ AFE 302 exchange signals with the ECG 18 and the bioimpedance sensor array 307. The GSR AFE 304 may exchange signals with the GSR sensor array 305. And the optical sensor AFE 306 may exchange signals with the optical sensor array 301. In one embodiment, the GSR AFE 304, the optical sensor AFE 306, the accelerometer 314, and the pressure sensor 316 may be coupled to the ADC 310 via bus 320. The ADC 310 may convert a physical quantity, such as voltage, to a digital number representing amplitude.

In one embodiment, the ECG and BIOZ AFE 302, memory 312, the processor 308 and the ADC 310 may be components of a microcontroller 322. The processor 308 in one embodiment may comprise a reduced instruction set computer (RISC), such as a Cortex 32-bit RISC ARM processor core by ARM Holdings, for example. In one embodiment, during operation the sensor computing unit 28 may collect and store the sensor data in memory 312 for subsequent transfer to the base computing unit 20.

Also depicted as part of the processor 308 is confidence indicator (CI) engine 400. In other embodiments, the CI engine 400 may be considered part of the processor in the base computing unit 20, of another processor (not shown) in the sensor module 14, or of another processor (not shown) in the wearable sensor platform 10. The CI engine 400 may be implemented as instructions executed on the processor 308 and is used to determine a confidence indicator for physiological data measured using the sensor module 14.

In particular, the CI engine utilizes artifact data captured separately from the data for the physiological parameter of interest and/or noise data inherent in the physiological data to determine a level of confidence that can be had in the processed physiological data signal. As used herein, noise data is the portion of the physiological data inherent in the measurements of the physiological parameter of interest and estimated (at least in part) using the measurements of the physiological parameter of interest. For example, in determining heartbeats (the physiological parameter of interest), the noise data is inherent in the PPG measurements performed by the optical sensor array 301. The amount of this noise may be determined using signal processing of the PPG data from the optical sensor array 310. Artifact data may be separately measured from the physiological parameter of interest. The artifact data may be measured by the same sensor unit(s) 24 measuring the physiological data and/or by separate sensor unit(s). Artifact data can be correlated to the physiological parameter of interest and may affect the measurements of the physical parameter of interest. To this extent, artifact data can be utilized to measure (or estimate) the artifacts' contribution to the noise. However, nothing prevents the "artifact" data to be physiological data related to another physiological parameter. In the PPG data example above, acceleration data (artifact data) may be measured by the accelerometer 314. The motion indicated by the acceleration data may contribute to the noise in the PPG data used in determining heart rate. This contribution may be determined, for example, by correlating peaks in the frequency spectrum of the acceleration data with peaks in the PPG data. In determining the level of confidence in the heart rate measurement, one or both of noise data as determined from the physiological data and artifact data from the accelerometer 314 can be used. For example, the signal-to-noise ratio in the PPG measurements (noise data) and the acceleration data (artifact data) can both be used in determining the level of confidence in the detection of heartbeats (physiological parameter of interest). Further, note that determination of the signal-to-noise ratio may involve the use of processed artifact data. An indicator of this confidence level can then be provided to the user of the wearable sensor platform 10.

The CI engine 400 may use a particular signal processing algorithm, or measure, to determine the level of noise and thus the confidence in the data. For example, absolute limits on the magnitude of the noise and/or artifacts, the frequency characteristics (e.g. number of peaks in a frequency spectrum or the overlap between peaks from the physiological data and the artifact data in the frequency spectrum), standard deviation threshold(s), peak-to-peak noise and/or artifact threshold(s), ratio threshold(s), a cyclic nature of the noise/artifact, identification of a dominant frequency component which exists above a certain noise/artifact level (as determined by an average noise/artifact level and/or a specified threshold noise/artifact level) and/or other characteristics may be used to determine the confidence indicator. In some embodiments, a filter including but not limited to a time domain filter, a frequency domain filter, a Bayesian filter, a Kalman filter, a template-based filter, and/or another type of filter may be used to determine the level of confidence in the data. In an embodiment, a function maximization or minimization scheme may be used. For example, a "cost" function associated with a certain parameter or set of parameters related to noise and/or signal quality may be defined. This cost function may then be maximized or minimized. Other signal processing and/or noise recognition algorithms used by the CI engine 400. Further, processing of artifact data by the CI engine 400 may inform its signal processing and vice versa prior to a final calculation of the confidence indicator. In the heart rate/PPG example above, the artifact data from the accelerometer (e.g. peaks in the frequency spectrum) may be used to remove motion artifacts prior to determining the signal-to-noise ratio for the PPG data. The particular algorithms used may depend upon the type of noise data, artifact data, and/or the type of physiological data being analyzed by the CI engine 400. Thus, operation of the CI engine 400 is not depend upon a particular heuristic used to analyze noise.

Once received by the CI engine 400, noise, artifact and/or physiological data may be processed to produce quantities including but not limited to a magnitude, a standard deviation, a mean, a median, a mode, a Fourier transform, a Hartley transform, and/or other processed data. The processed data may be treated in various domains including, but not limited to, inverse space, phase space, time space, and frequency space. For example, a Fourier transform, which may be discrete or continuous, may be used to find and filter out certain features in the noise and/or artifact data as a function of frequency and/or time. The data may be further processed by the CI engine 400 to be output as, for example, a scalar figure of merit (e.g. a peak value over a standard deviation) and analyzed in relation to threshold value(s). This scalar confidence indicator may be time dependent and presented to the user in a number of ways including, but not limited to, visually, physically and/or acoustically. For example, based on the relationship between the scalar confidence indicator and the relevant threshold(s) over a certain time period, a particular color (red, orange, or green) may be selected for display, a waveform for the physiological data may be displayed in a particular manner (portions of the waveform having different color(s), background(s) and/or line format(s)), text having different color(s) and/or formats may be used, an alarm may be sounded and/or the wearable sensor platform 10 may be placed in a vibration mode.

In an embodiment, the confidence indicator produced by CI engine 400 is used to adapt the presentation of the physiological data to the user in real time. For example, based on the confidence indicator, aspects of the display may be turned on and/or off. Various visualization characteristics such as line width, line style, line color, background color, and other aspects of the data being presented to the user may be changed in real time to update the user as to the current level of confidence in the physiological data. The audio and physical confidence indicators discussed above may also be provided using the processed noise and/or artifact data. In some embodiments, low confidence portions of the physiological data signal (e.g. the confidence indicator below a threshold) may be replaced, or concealed. The replacement may be performed using, for example, interpolated data, average data, a null signal and/or some other mechanism. The filter(s) used in processing the physiological data may also be selected based on the confidence indicator. In some embodiments, the confidence indicator may indicate that the signal(s) are to be switched on and/or off (e.g. a signal providing redundant information may be switched off). The mode of operation of the wearable sensor platform 10 may be changed based on the confidence indicator.

The CI engine 400 may estimate the noise inherent in the physiological (e.g. raw) data and use this estimate in presenting the physiological data signal to the user. For example, this estimated noise may be subtracted off of the physiological data during data processing. Whether or not the noise is to be subtracted off of the physiological data may be determined at least in part by the confidence indicator. For example, a filtering algorithm may be used to remove or substantially remove some noise and/or artifacts from the data. In one embodiment, a filtering algorithm may use the noise data to predict and/or estimate the noise component of the physiological data for purposes of reducing or substantially eliminating unwanted noise from the data. Similarly, artifacts contributing to the noise in the physiological data may be estimated and subtracted from the physiological data. For example, a filtering algorithm may use the artifact data to predict and/or estimate the artifacts in the physiological data for purposes of reducing or substantially eliminating the artifacts. Noise and/or artifacts in the physiological data may be predictively filtered out based on data acquired as or before the physiological data are taken. Alternatively, previously measured physiological data may have the noise contributions retroactively subtracted out. Noise in the data may be removed following its acquisition, in real-time during acquisition, or pre-removed ahead of its acquisition for example by filtering certain frequencies to prevent their measurement. Filtering of the physiological data to remove unwanted noise and/or artifacts may be done in the time domain, frequency domain, or other domain as appropriate. As an example, a time domain filter may be practical for removal of artifacts when the data has a waveform that is cyclic in nature. If, however, the noise and/or artifact data is too large in magnitude (confidence level in physiological data too low) or the noise and/or artifact data is too low in magnitude (confidence in physiological data very high) it may be undesirable to expend computing resources in subtracting the noise/artifacts from the physiological data. Thus, the confidence indicator generated by the CI engine 400 may be used not only to process the noise and/or artifact data and remove such data from the physiological data, but also to determine whether to remove such data from the physiological data.

Data which are deemed to be unusable based on the confidence indicator may be concealed. In some embodiments, noise levels and/or artifacts, or an estimation thereof, may be determined by the CI engine 400 as part of the process of calculating a confidence indicator. Based on the confidence indicators, a determination is made as to whether or not a concealment process need be implemented (i.e. to prevent motion artifacts from disturbing further processing such as, for example, baseline filtering). The concealment process may include using interpolated values, previously measured values, averages values, providing a null signal for the unacceptable portion, or otherwise concealing the unacceptable data. Based on the confidence indicators determined by the CI engine 400 various action(s) may thus be taken by the platform 10.

The CI engine 400 may also make use of identifiers in determining the confidence indicator. The artifact data and physiological data (including its inherent noise) received from the sensor unit(s) 24 may contain identifying data which may include, but is not limited to, a timestamp and/or a location coordinate which may be used for purposes of data synchronization and/or integration. Sensor data may have an additive, subtractive, or other relational effect on other sensor data which may be time and/or location dependent.

As mentioned above, the CI engine 400 may determine the confidence indicator using data from one or more of the sensor units 24. The CI engine 400 may also utilize the physiological data for the physiological parameter of interest, noise data, artifact data and/or other data to calculate the confidence indicator. For example, the physiological data of interest may be provided from a sensor unit 24 to the CI engine 400. The CI engine 400 may determine the signal-to-noise ratio (SNR) inherent in the physiological data during data processing. Note that the CI engine may remove, suppress or otherwise account for artifacts as part of this process. The magnitude of the SNR may be used as a confidence indicator or may be part of the calculation of another confidence indicator for the physiological data. The CI engine 400 may thus provide a signal quality estimation for the physiological data being measured.

The same sensor unit(s) 24 that capture the physiological data may also provide artifact data to the CI engine 400 for artifacts distinct from the physiological data. For example, electrode-tissue impedance (ETI) may change for reasons unrelated to the physiological data of interest. In an ECG, for example, the user's finger may move with respect to the ECG sensor unit 309 (e.g. with respect to the clasp if an ECG sensor for the unit 309 is on the clasp). The user's skin may also stretch or otherwise change in the region of the sensor 309. Such motion may result in artifacts corresponding to a change in ETI. The ETI may be determined by a sensor unit passing a small current through and determining the impedance of the tissue surrounding the sensor unit. This measurement of ETI is separate from the measurement of physiological data but performed by the same sensors. For example, the ECG sensor array 309 performs both the ECG measurement and the corresponding ETI measurement. The CI engine 400 may use the ETI (artifact data) to determine the level of confidence in the ECG (physiological data). To do so, the CI engine 400 may correlate the ETI (artifact) data with the ECG (physiological) data. Once the data are correlated, a level of confidence in the physiological (ECG) data may be determined based on characteristics of the artifacts (ETI) data. Thus, the artifact data may be captured by the same sensor unit 24 that measures physiological data and used to provide a confidence indicator for the physiological data.

The CI engine 400 may use data from other sensor unit(s) 24 to determine the confidence indicator. To do so, the CI engine 400 may correlate the physiological data being measured by one sensor unit 24 with the artifact data from another sensor unit 24. If a sufficient correlation exists, the confidence in the physiological data may be low. For example, in the ECG measurements discussed above, motion may contribute to artifacts to the noise in the ECG data. These motion artifacts may be due to motion of the sensor unit(s) 309 with respect to the user as well as motion of the entire wearable sensor platform 10 because of movement of the user him/herself. For example, the swinging motion of the arm may result in cyclic noise in the physiological data from the ECG sensors 309. The motion of the user with respect to the ECG sensor array 309 may be accounted for at least in part by ETI as discussed above. In order to assess remaining motion artifacts, artifact data in the form of acceleration data may be taken from the accelerometer 314. The acceleration data from accelerometer 314 may be correlated with the ECG data from the ECG sensors 309. For example, the accelerometer data and ECG data may be transformed to the frequency spectrum. If the accelerometer data and the ECG data have extraneous peaks at the same frequency, a correlation between the motion of the hand and the ECG data may be determined and a corresponding confidence indicator provided.

Similarly, motion artifacts may be at issue in PPG measurements performed by the optical sensor array 301 and used in determining pulse. For the PPG measurement, the movement of the band 16 with respect to the arm may change the position of the optical sensor array 301 with respect to blood vessels. Swinging of the arm may result in cyclic noise, for example due movement of the band 16 with respect to the arm. In other embodiments, such as a chest band, movement of the heart within the chest may also be a source of noise for the PPG measurement. In order to assess these motion artifacts, artifact data in the form of acceleration data may be taken from the accelerometer 314. The accelerometer data may be correlated with the PPG data captured by the optical sensor array 301. Based on this correlation, the artifacts due to motion, and thus the motion artifacts' contribution to the noise in the PPG data, may be determined and a level of confidence in the heart rate being calculated and provided to the user.

In addition, note that in determining the output signal for a particular physiological parameter, types of physiological data and/or artifact data may be used. For example, a determination of heart rate may use a detection of beats using both ECG data (physiological data) from the ECG sensor Array 309 and PPG data (physiological data) from the optical sensor array 301. For the ECG data, artifact data may come from an ETI measurement made by ECG sensor array 309 and acceleration data made by the accelerometer 314. For the PPG data, artifact data may come from the acceleration data made by the accelerometer 314. A signal-to-noise ratio may be determined for the detection of heart beats for both the PPG data and the ECG data. The heart rate may be determined based on both the PPG data and the ECG data. The confidence indicator may thus be determined based on the PPG data, the ECG data and artifact data (acceleration and ETI) for both. Thus, the CI engine may combine multiple sources and types of physiological data (and thus noise data) with appropriate source(s) of artifact data to determine confidence indicator(s) for the physiological parameter of interest.

The CI engine 400 may also combine multiple confidence indicators in order to determine an overall confidence indicator for the physiological data. In the ECG example above, the CI engine may use an estimate for noise in the ECG data measured by the ECG sensors 309 (physiological data including noise), the ETI measured by the ECG sensors (artifact data) and the acceleration data (artifact data) measured using the accelerometer 314 in order to determine an overall confidence indicator for ECG data. In some embodiments, an ETI confidence indicator, a motion/acceleration confidence indicator and SNR may simply be combined to provide an overall confidence indicator. In other embodiments, different, fewer and/or additional confidence indicators may be combined for the overall confidence indicator. However, some sources of noise and/or artifacts may be more important than others. In some embodiments, therefore, contributions may be weighted. A combination of confidence indicators may also result in a mid-level confidence indicator due to a high degree of confidence in the SNR (i.e. high SNR) and a very low degree of confidence due to motion artifacts (a high degree of motion induced noise). In some embodiments, certain confidence indicators being above or below a threshold may result in the overall confidence threshold being above or below the threshold. For example, a very low SNR may result in a confidence indicator for a low level of confidence in the physiological data even if there is a high degree of confidence that no motion artifacts exist. Further, different methods of combining confidence indicators may be used for different types of physiological data and/or for different conditions in which the wearable sensor platform 10 operates.

The confidence indicator from the CI engine 400 and the physiological data signal are then presented to the user of the wearable device platform 10. How the data are presented may be determined by the confidence indicator. For example, a high low confidence level (e.g. confidence indicator above or below a particular threshold), may result in the physiological data signal being displayed in a default manner. For some data signals, this may be a font of a particular size, color or format. For other physiological data signals, the waveform corresponding to the signal may have a default format (e.g. color, line thickness or type, background color or type). In other cases, the high confidence in the data may be indicated in another manner (e.g. a green light). Other levels of confidence (e.g. confidence indicator being below, above and/or between threshold(s)) may result in some or all of the physiological data being displayed in another manner. For some data signals, this may be a font of a different size (e.g. smaller), color (e.g. red) or format (e.g. unbolded or in italics). The portion of the waveform for the data signal having a different confidence level may have a different color or line format, may be concealed or estimated (e.g. replaced by interpolated or other data), may have a different background color or be indicated in another manner. In other cases a different colored light (e.g. red or orange) may be used. Thus, using the sensor module 14, the physiological data from the sensor units 24 may not only be processed and provided to the user as a data signal such as a numerical heart rate or waveform, but also may be accompanied by an indication in the level of confidence for the physiological data.

Figure 7:
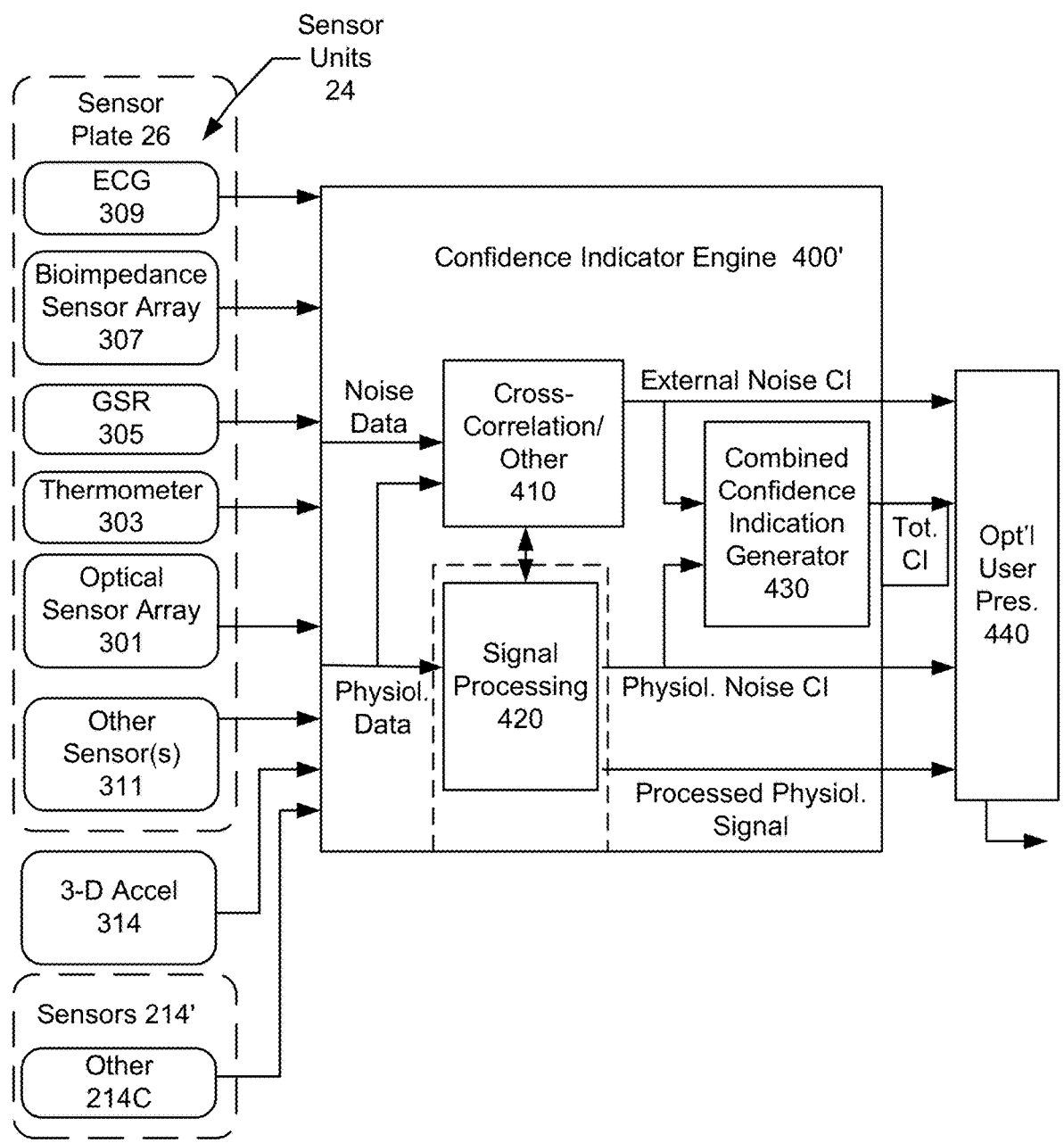
FIG. 7 is a block diagram of an exemplary embodiment of a confidence indicator engine for a modular wearable sensor platform.

FIG. 7 is a block diagram of an embodiment of a CI engine 400' as well as the sensor units 24 and 214 for a modular wearable sensor platform 10. The CI engine 400', sensor units 24, sensor plate 26 and sensors 214 are analogous to the CI engine 400, sensor units 24, sensor plate 26 and sensors 214 and thus have similar labels. In the embodiment shown, the sensor units 24 may include an optical sensor array 301, a thermometer 303, a GSR sensor array 305, a BioZ sensor array 307, and an ECG sensor 309, other sensor(s) 311 and/or any combination thereof. Although a particular number sensors and sensor arrays are shown, another number of sensors/sensor arrays and/or different sensors/sensor arrays may be included. The sensors and/or arrays may be affixed to the sensor plate 26 or the band 16.

Also shown are accelerometer 314 and other sensors 214. In the embodiment shown, the accelerometer 314 is part of the sensor module 14. In other embodiments, the accelerometer 314 may instead be part of the base unit 20. The other sensor(s) 214C might include the thermometer 214B and/or other sensors located in the base computing unit 20.

The CI engine 400' may be implemented in software executable on a processor such as the processor 308 and/or hardware including but not limited to an application specific integrated circuit and/or processing unit. The CI engine 400' includes a cross-correlation noise processing module 410, signal processing module 420 and optional combined CI generator 430. Also shown is user presentation block 440 that may be part of the CI engine 400' or receive input(s) from the CI engine 400'. The signal processing module 420 may be part of the CI engine 400 or part of another module. Consequently, a dashed line is shown around the signal processing module 420.

The CI engine 400' has as inputs data from the sensor units 24, accelerometer 314 and other sensors 214. The specific signal(s) input to the modules 410 and 420 depend upon the physiological data being measured. For example, for ECG data, signals may be from the ECG sensors 309 (both ECG and ETI signals) and from the accelerometer 314. For PPG data, signals may be from the optical sensor array 301 and the accelerator 314. Other physiological data may use different and/or additional sensor(s). Thus, all sensors 214C, 314, 301, 303, 305, 307, 309, and 311 may provide data to the CI engine 400', but only particular signals are input to modules 410 and 420.

The signal processing module 420 receives as an input the physiological data from the sensor unit(s) 24 and/or other sensors 214. In addition, information from the block 410, discussed below, may be provided to the signal processing module 420. The physiological data corresponds to the physiological parameter of interest, such as heart rate, ECG, bioimpedance and/or other parameter. The signal processing module 420 may apply modeling, signal processing algorithms and/or other mechanisms to determine the physiological data signal from the raw physiological data input to the CI engine 420. The physiological data signal may be a waveform, a scalar such as heart rate or other representation of the physiological parameter of interest. As part of data processing the signal processing module 420 may also estimate the noise inherent in the physiological data. For example, an SNR may be determined. Thus, a confidence indicator (SNR) for the data itself may be output by the signal processing module 420. A physiological CI and a processed physiological signal are shown as being output by the signal processing block 420. In another embodiment, the signal processing module 420 may provide physiological features to the block 420, which may calculate SNR. In such an embodiment, the signal processing module 420 may be considered separate from the CI engine 400'. Further, the signal processing module 420 may receive information regarding artifacts from the module 410.

The physiological data (including inherent noise data) from the sensor unit(s) 24 and/or other sensors 214 and artifact data from the sensor unit(s) 24, accelerometer 314 and/or other sensors 214 are input to cross-correlation block 410. Data may also be provide by the signal processing block 420 to the cross-correlation block 410. Modeling and other data processing algorithms may be applied by the cross-correlation block 410 to determine the correlation between the artifact data and the physiological data. Other features of the artifact data may also be determined in cross correlation block 410. Thus, confidence indicator(s) for the artifact data and/or the correlation between the artifact data and the physiological data may be output by the cross correlation block 410. In some embodiments, one or both of the confidence indicators output by modules 410 and 420 may be directly provided, along with the physiological data signal, for the presentation to the user. In other embodiments, an overall, combined confidence indicator may be generated by module 430 using the confidence indicators from modules 410 and 420. In some embodiments, different weights may be applied to the confidence indicators from modules 410 and 420.

The combined, total confidence indicator (if any) provided by module 430, the physiological data signal and inherent noise confidence indicator provided by the module 420 as well as the external confidence indicator/artifact indicator provided by cross correlation module 410 may be used by the user presentation module to provide the data to the user. The processed signal may, for example, be a waveform, a number or other representation of the physiological data of interest. The user presentation module 440 may update the physiological data itself or the environment in which the data are presented in order to indicate the confidence level in the physiological data as expressed by the confidence indicator.

Figure 8:
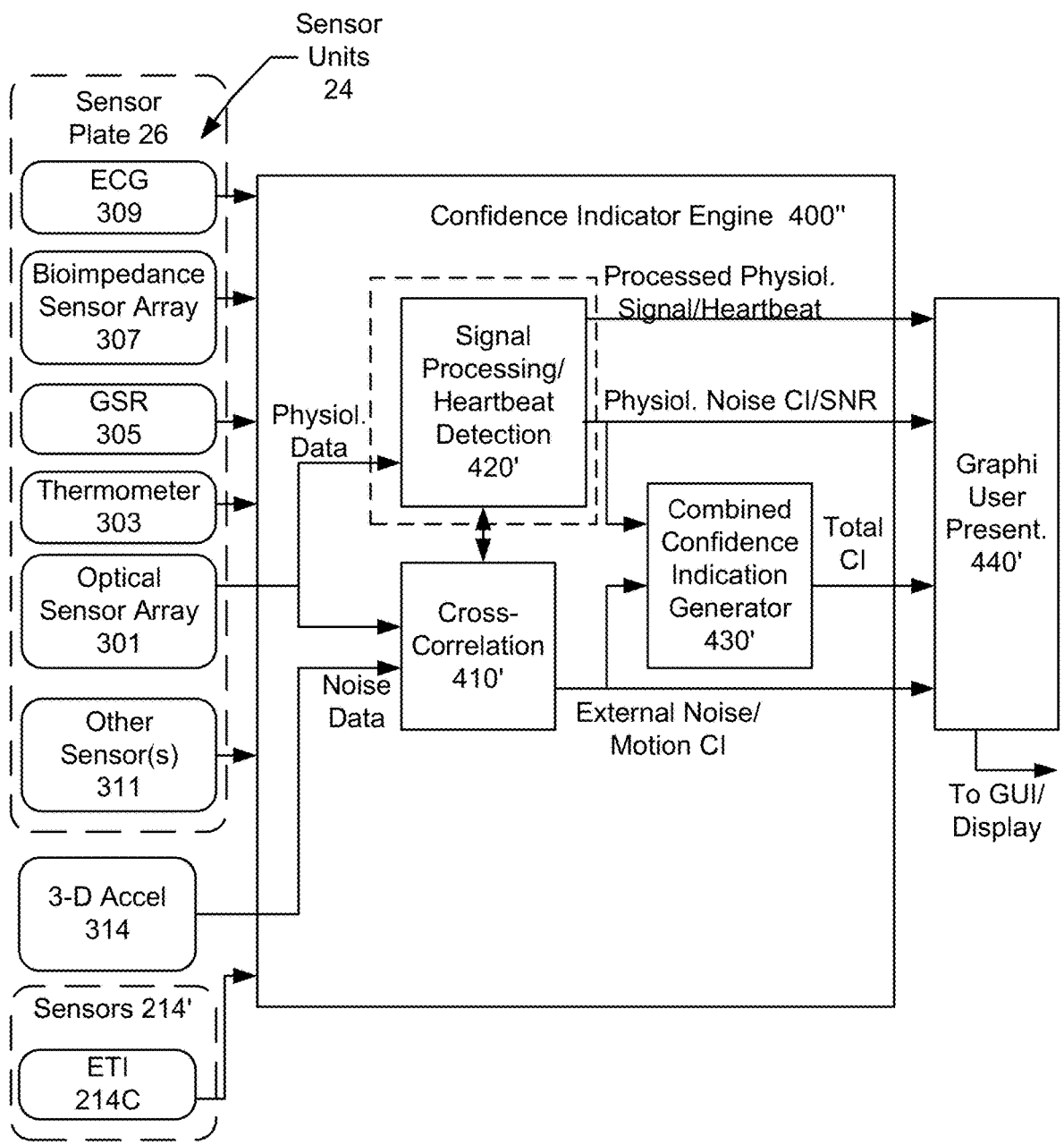
FIG. 8 is a block diagram of another exemplary embodiment of a confidence indicator engine for a modular wearable sensor platform.

FIG. 8 is a block diagram of another embodiment of a CI engine 400" as well as the sensor units 24 and 214 for a modular wearable sensor platform 10 as used to process a particular type of physiological data. The CI engine 400", sensor units 24, sensor plate 26 and sensors 214 are analogous to the CI engine 400/400', sensor units 24, sensor plate 26 and sensors 214 and thus have similar labels. In the embodiment shown, the sensor units 24 may include an optical sensor array 301, a thermometer 303, a GSR sensor array 305, a BioZ sensor array 307, and an ECG sensor 309, other sensor(s) 311 and/or any combination thereof. Although a particular number sensors and sensor arrays are shown, another number of sensors/sensor arrays and/or different sensors/sensor arrays may be included. The sensors and/or arrays may be affixed to the sensor plate 26 or the band 16.

The CI engine 400" is configured for PPG data. Thus, the CI engine 400" uses data input from the optical sensor array 301 and the accelerometer 314. The physiological (PPG) data are provided to the signal processing/heartbeat detection module 420' that corresponds to the signal detection module 420. The module 420' outputs an SNR as well as the heartbeat (processed signal) and/or other physiological features detected. The PPG data from the optical sensors 301 as well as the acceleration (artifact) data from the accelerometer 314 are input to the cross-correlation module 410'. The cross-correlation module may be used to determine correlations between the artifact (acceleration) data and the physiological (PPG) data. The module 410' determines correlations between the accelerometer and PPG data, for example by detecting cyclic motion artifacts in the PPG data that match the accelerometer data and determining the severity of such motion artifacts. In some embodiments, the module 410' may also determine SNR.

The combined confidence indication generator 430' combines the SNR/output of the module 420' and confidence indicator from module 410' to a total confidence indicator. The confidence indicators and processed physiological signal (heartbeat) are thus generated from the raw data. The combined, total confidence indicator (if any) provided by module 430', the heartbeat and SNR provided by the module 420' as well as the external confidence indicator provided by cross correlation module 410' may be used by the user presentation module to provide the data to the user. The processed signal may, for example, be a waveform indicating a number of heartbeats per unit time or other representation of the physiological data of interest. The user presentation module 440 may update the physiological data itself or the environment in which the data are presented in order to indicate the confidence level in the physiological data as expressed by the confidence indicator. For example, a light indicating the level of confidence in the data, a heart rate color or other representation of the confidence indicator may be used.

Figure 9:
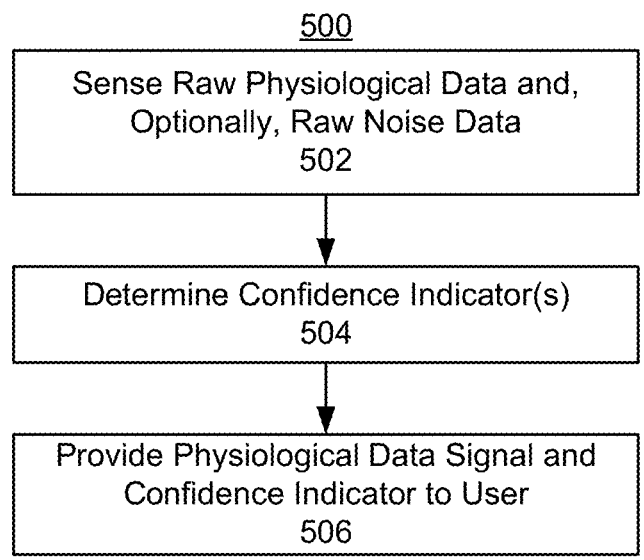
FIG. 9 is a flow chart depicting an exemplary embodiment of a method for providing a user with physiological data and a confidence indicator using a wearable sensor platform.

FIG. 9 is a flow chart depicting an embodiment of a method 500 for providing a user with physiological data and a confidence indicator using a wearable sensor platform. The method 500 is described in the context of the wearable platform 10 and CI engine 400. In other embodiments, the method 500 may be performed using other system(s). Some steps may be omitted, combined, interleaved, performed in another order and/or include substeps.

Referring to FIGS. 7 and 9, physiological data (including its inherent noise data) are sensed using the appropriate sensor(s) 24, via step 502. In embodiments in which the module 410/410' is used, artifact data are measured separately from the physiological data. This data capture may be performed using the same sensor as sensed the physiological data and/or other sensors. For example, for ETI, the same sensor(s) may be used. For other noise data, such as motion/acceleration, a separate sensor may be used.

The confidence indicator(s) for the physiological data are determined, via step 504. Step 504 may be considered to include processing of the physiological signal itself, processing of the noise and artifact data, as well as correlating the artifact data with the physiological signal data. Modules 410/410' and/or 420/420' may thus be used in performing step 504. In addition, an overall confidence indicator may be calculated in module 430/430' as part of step 504.

The processed physiological data signal and confidence indicator(s) are provided to a user via the wearable sensor platform 10, via step 506. Step 506 may include using various visual, auditory and/or physical clues to indicate the level of confidence in the physiological data expressed by the confidence indicator. Thus, using the method 500, physiological data for the wearable sensor platform 10 may be captured, processed, assessed, and presented to the user along with the assessment.

Figure 10:
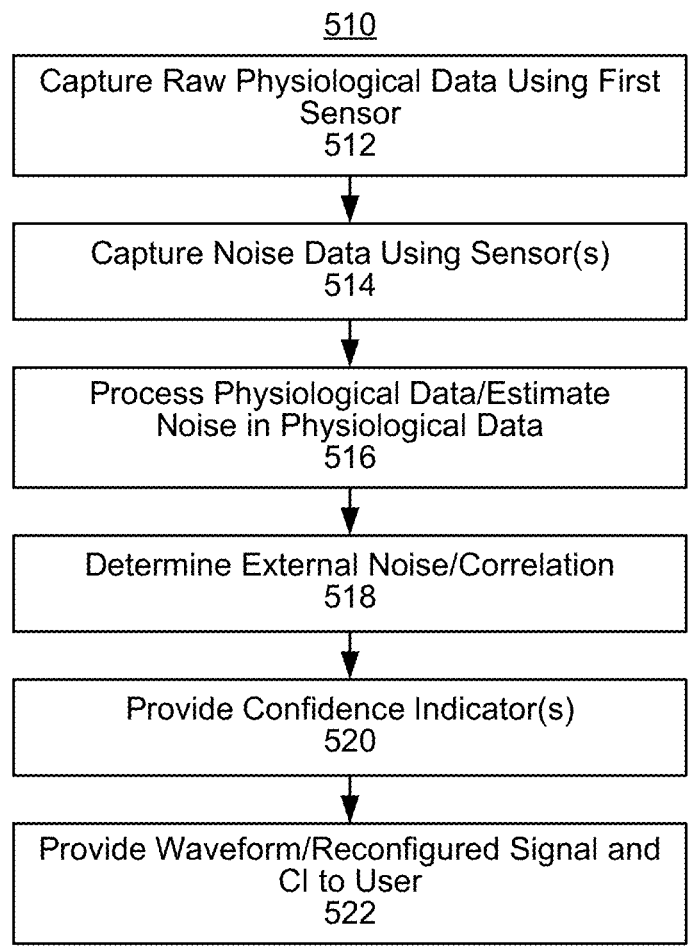
FIG. 10 is a flow chart depicting an embodiment of a method for providing a user with physiological data and a confidence indicator using a wearable sensor platform.

FIG. 10 is a flow chart depicting an embodiment of a method 510 for providing a user with physiological data and a confidence indicator using a wearable sensor platform. The method 510 is described in the context of the wearable platform 10 and CI engine 400. In other embodiments, the method 510 may be performed using another system. Some steps may be omitted, combined, interleaved, performed in another order and/or include substeps. The method 510 may be used when data from multiple sensors are used.

Referring to FIGS. 7 and 10, physiological data are sensed using a first sensor unit 24, via step 512. This data may include parameters for bioimpedance, ECG, or PPG data. Artifact data is also separately captured using one or more sensors, via step 514. The data sensed in step 514 may include artifact data that can be sensed with the same sensor unit 24, such as ETI. Artifact data that may be measured using other sensors is also captured in step 514, such as acceleration data. Steps 512 and 514 may take place simultaneously/over the same time period and may each involve several sampling steps that may be repeated in parallel.

The physiological data captured in step 512 is processed using module 420, via step 516. The physiological data signal, such as ECG or heart rate, is thus obtained. Step 516 may be performed using known data processing algorithms appropriate for the physiological data of interest. As part of the data processing, a noise inherent in the physiological data may be obtained. For example, a SNR may be calculated in step 516. The SNR may correspond to a confidence indicator determined by module 420 in step 516. Alternatively, the SNR may be determined separately if determination of the confidence indicator is separate from signal processing.

Correlations between the artifact data and the physiological data are determined by module 410, via step 518. Step 518 may be performed using modeling, known algorithms such as Fourier transforms and other/or other mechanisms. The module 410 may also provide a confidence indicator for the correlated artifact data in step 520. Note that steps 516 and 518 may be interleaved. Thus, correlations between the artifact data and the physiological data may be used in processing the physiological data in step 516. Similarly the processed physiological data may be used in determining the correlations with the artifact data in step 518

Based on the SNR, the correlations and the physiological data, confidence indicators may be determined, via step 520. Step 520 may include providing a total confidence indicator based on the above data signals and/or the confidence indicators determined in steps 516 and 518.

The processed physiological data signal and confidence indicator(s) are graphically or otherwise provided to user, via step 522. Thus, using the method 510, physiological data for the wearable sensor platform 10 may be captured, processed, assessed, and presented to the user along with the assessment.

Figure 11:
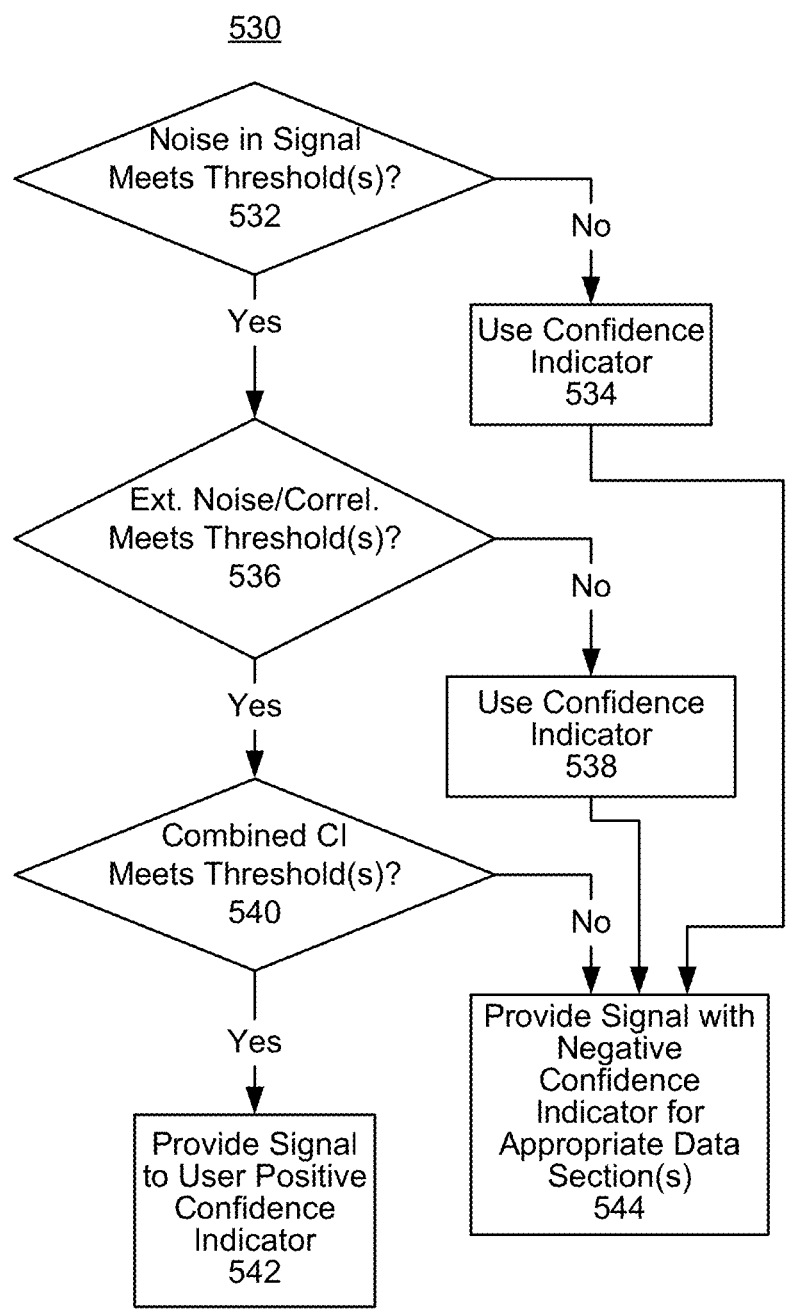
FIG. 11 is a flow chart depicting an embodiment of a method for providing a user with physiological data and a confidence indicator using a wearable sensor platform.

FIG. 11 is a flow chart depicting an embodiment of a method 530 for providing a user with physiological data and a confidence indicator using a wearable sensor platform. More specifically, the method 530 depicts one embodiment of how the confidence indicators may be combined to determine how data may be altered to represent the confidence indicator. Confidence indicators may be calculated in another manner. The method 530 is described in the context of the wearable platform 10, CI engine 400 and the module 440. In other embodiments, the method 510 may be performed using another system. Some steps may be omitted, combined, interleaved, performed in another order and/or include substeps. The method 530 may be used when data from multiple sensors are used.

It is determined how the noise in the physiological data compare with thresholds for the noise data, via step 532. For example, the module 440 may compare the SNR or other with threshold(s) or determine the relationship of the absolute magnitude of the noise in the physiological data with other thresholds. If this is not within certain thresholds, then the confidence indicator that alters how the physiological data are displayed is selected, via step 534. Step 534 may be considered to indicate that at least a portion of the data are changed from a default for presentation to the user.

If the noise in the physiological data does meet the threshold(s), then it is determined whether the correlation between the physiological data and the artifact data meets certain thresholds, via step 536. Step 536 may also determine whether the artifact data itself meets particular thresholds. For example, step 536 may determine whether the correlation between the noise data and physiological data is less than a certain threshold or if the magnitude of the noise is within certain limits. If not, then a confidence indicator that changes how the physiological data are presented to the user is selected, via step 538. Step 536 indicates that at least a portion of the data are changed for presentation to the user. Note that steps 536 and 538 may be switched with steps 532 and 534 in one embodiment. The order in which these blocks are performed may be changed. What is desired is a separate indication of the levels of artifacts and noise in the data and a mechanism for determining and accounting for confidence indicators based separately on these data sets.

The combined confidence indicator is calculated and compared to appropriate threshold(s), via step 540. For example, combined confidence indicator may be a weighted or unweighted mean of the confidence indicators from steps 534 and 538. If the combined confidence indicator meets the thresholds, then the confidence level in the data may be sufficiently high. Thus, in step 542 the data are presented to the user in a default fashion. If the combined confidence indicator does not meet thresholds or the steps 534 or 538 have been performed, then the physiological signal data are provided to the user with an indication that the confidence level is low. Through step 544, the module 440 may use the three confidence indicators indicating a low confidence from steps 534, 538 and 540 to provide various visual, auditory and/or physical cues to the user regarding the output signal. Thus, the user may be informed of the level of confidence in the physiological data signals.

Figure 12:
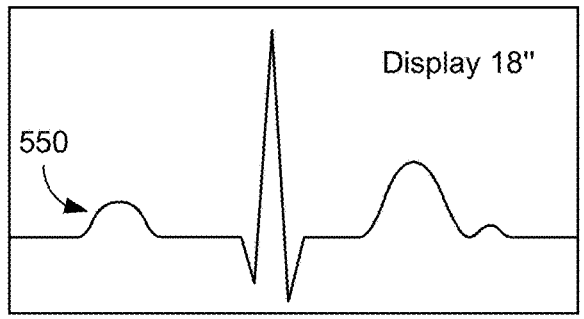
FIGS. 12-17 are diagrams depicting various physiological data and confidence indicators.
Figure 13:
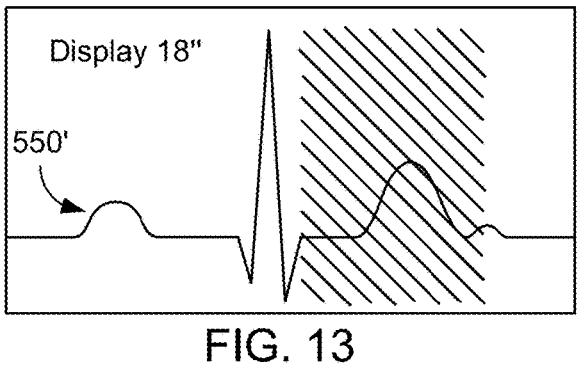
Figure 14:
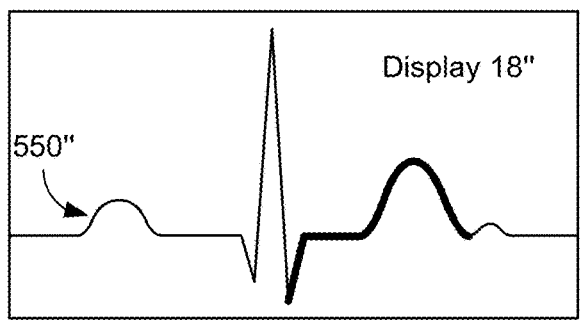
Figure 15:
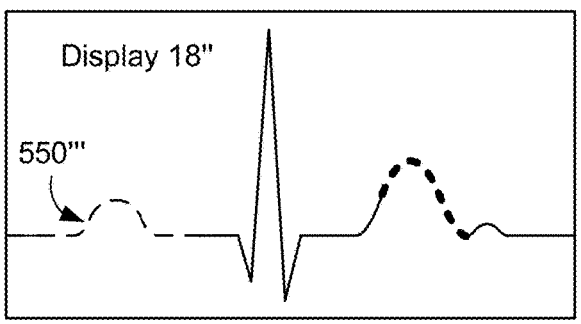
Figure 16:
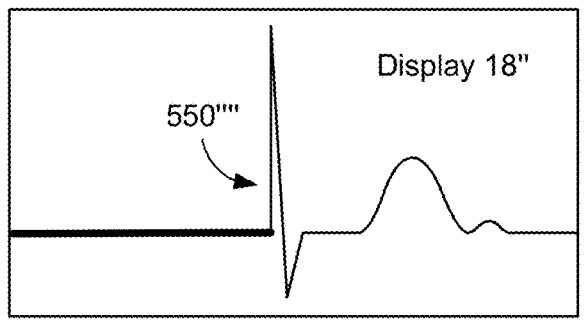
Figure 17:
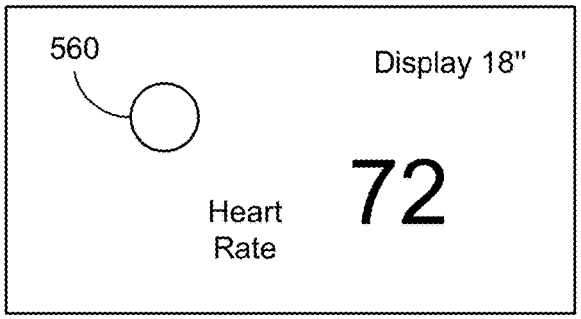

FIGS. 12-17 are diagrams depicting various physiological data and confidence indicators that are graphically provided to the user. FIGS. 12-17 thus depict various view of the display 18. In FIGS. 12-17, the waveform for ECG physiological data is depicted. In FIG. 12, the waveform 550 is one in which the confidence indicator corresponds to a high level of confidence. Thus, a default background and line format are present. FIG. 13 depicts a waveform 550' for ECG physiological data in which a portion of the background has been cross-hatched to denote data for this portion of the waveform having a confidence indicator corresponding to a lower level of confidence. In alternate embodiments, the cross-hatched region may correspond to a confidence indicator denoting a particularly high level of confidence. FIG. 14 depicts a waveform 550" for ECG physiological data that has a portion of the data with a thicker line. The thicker portion of the line might correspond lower level of confidence in his part of the physiological data. For example, the ECG data may have been replaced with data interpolated from prior ECG or model ECG data. FIG. 15 depicts a waveform 550''' for ECG data that has thee data portions. One, central portion has the default line format. One portion has a dashed line format. Another portion of the waveform 550''' is both dashed and has a larger line width. Thus, the display 18 of FIG. 15 represents confidence indicators for three different levels of confidence. The section having the dashed and thicker line format may have the lowest confidence level, the dashed line may have the next highest confidence level, and the plain (central) portion may have the highest level of confidence for the plot 550'''. FIG. 16 depicts a waveform 550'''' that has a portion of the signal blanked and represented by a thicker line. This portion of the data may have a confidence indicator that is particularly low, resulting in concealment of the actual data. FIG. 17 depicts heart rate data on the display 18. Also shown is a region 560 that may be colored to reflect the confidence indicators. For example, red, green and orange may be used to fill the region 560 for low quality, high quality and moderate quality, respectively. Note that in other embodiments and/or for other physiological signals, the formats may be changed in a different manner. Thus, the confidence in the data may be determined and presented to the user A method and system for providing a confidence indicator for a physiological data signal has been disclosed. The present invention has been described in accordance with the embodiments shown, and there could be variations to the embodiments, and any variations would be within the spirit and scope of the present invention. Accordingly, many modifications may be made by one of ordinary skill in the art without departing from the spirit and scope of the appended claims.

We claim:

1. A method for providing physiological data to a user of a wearable sensor platform, comprising:
    capturing data for the user using at least one sensor in the wearable sensor platform, the wearable sensor platform including a band worn around a portion of the user, the capturing the data including sensing physiological data captured by a physiological sensor of the at least one sensor and sensing artifact data, a portion of the artifact data being captured by an artifact data sensor different from the physiological sensor, the artifact data sensor being a motion sensor, the portion of the artifact data including motion data, the motion data being for motion of the motion sensor of the wearable sensor platform together with the portion of the user, the artifact data also including data specific to motion of the motion sensor with respect to skin of the user, the data specific to motion of the motion sensor with respect to the skin being captured by a sensor different from the motion sensor;
    determining a confidence indicator for the data based on the artifact data including the motion data from the motion sensor and the data specific to motion of the motion sensor with respect to the skin of the user from the sensor different from the motion sensor; and
    providing a physiological data signal corresponding to the physiological data and the confidence indicator to the user on the wearable device platform, thereby indicating to the user a confidence level for the physiological data.

2. The method of claim 1, wherein the providing the physiological data signal and the confidence indicator further includes:
    correlating the artifact data with the physiological data to determine an artifact confidence indicator, the confidence indicator including the artifact confidence indicator.

3. The method of claim 2, wherein the confidence indicator denotes whether a correlation between the artifact data and the physiological data is above a threshold.

4. The method of claim 3, wherein the determining the confidence indicator further includes:
    providing a total confidence indicator based on a first confidence indicator for the physiological data and the artifact confidence indicator.

5. The method of claim 1, wherein the motion sensor is an accelerometer.

6. The method of claim 5, wherein the motion sensor is an accelerometer.

7. A wearable sensor platform comprising:
    a band;
    a plurality of sensors coupled to the band, the plurality of sensors for capturing data for a user, the plurality of sensors including a physiological sensor for sensing physiological data and an artifact data sensor for capturing a portion of artifact data, the artifact data sensor being different from the physiological sensor, the data including the physiological data and the artifact data, the artifact data sensor being a motion sensor, the portion of the artifact data including motion data, the motion data being for motion of the motion sensor of the wearable sensor platform together with the portion of the user, the artifact data also including data specific to motion of the motion sensor with respect to skin of the user, the data specific to motion of the motion sensor with respect to the skin being captured by a sensor different from the motion sensor;
    a processor coupled to the plurality of sensors, the processor configured to receive the physiological data and the artifact data, determine a confidence indicator for the data based on the artifact data including the motion data from the motion sensor and the data specific to motion of the motion sensor with respect to the skin of the user from the sensor different from the motion sensor, and provide a physiological data signal corresponding to the physiological data and the confidence indicator to the user via the wearable device platform, thereby indicating to the user a confidence level for the physiological data.

8. The wearable sensor platform of claim 7, wherein the processor determines the confidence indicator by correlating the artifact data with the physiological data to determine an artifact confidence indicator, the confidence indicator including the artifact confidence indicator.

9. The wearable sensor platform of claim 8, wherein the confidence indicator denotes whether a correlation between the artifact data and the physiological data is above a threshold and wherein the processor further provides a total confidence indicator based on a first confidence indicator for the physiological data and the artifact confidence indicator.

10. The wearable sensor platform of claim 7, wherein the motion sensor is an accelerometer.

11. An executable software product stored on a non-transitory tangible computer-readable storage medium containing program instructions for providing physiological data to a user of a wearable sensor platform, the program instructions for:
receiving data for the user, the data captured using at least one sensor in the wearable sensor platform, the data including physiological data captured by a physiological sensor of the at least one sensor and artifact data, a portion of the artifact data being captured by an artifact data sensor different from the physiological sensor, the artifact data sensor being a motion sensor, the portion of the artifact data including motion data, the motion data being for motion of the motion sensor of the wearable sensor platform together with the portion of the user, the artifact data also including data specific to motion of the motion sensor with respect to skin of the user, the data specific to motion of the motion sensor with respect to the skin being captured by a sensor different from the motion sensor;
determining a confidence indicator for the data based on the artifact data including the motion data from the motion sensor and the data specific to motion of the motion sensor with respect to the skin of the user from the sensor different from the motion sensor; and
providing a physiological data signal corresponding to the physiological data and the confidence indicator to the user on the wearable device platform, thereby indicating to the user a confidence level for the physiological data.

12. The executable software product of claim 11, wherein the instructions for providing the physiological data signal and the confidence indicator further include instructions for:
correlating the artifact data with the physiological data to determine an artifact confidence indicator, the confidence indicator including the artifact confidence indicator.

13. The executable software product of claim 12, wherein the confidence indicator denotes whether a correlation between the artifact data and the physiological data is above a threshold.

14. The executable software product of claim 13, wherein the instructions for determining the confidence indicator further include instructions for:
providing a total confidence indicator based on a first confidence indicator for the physiological data and the artifact confidence indicator.

15. The executable software product of claim 11, wherein the motion sensor is an accelerometer.

* * * * *